United States Patent [19]

Fischer et al.

[11] Patent Number: 4,801,601

[45] Date of Patent: Jan. 31, 1989

[54] N-SUBSTITUTED POLYGLYCIDYL URAZOLE COMPOUNDS, PROCESSES FOR THEIR PRODUCTION AND PHARMACEUTICAL PREPARATIONS

[75] Inventors: Herbert Fischer, Düsseldorf; Brigitte Hase, Erkrath; Hinrich Möller, Monheim; Hans-Christoph Wilk, Neuss; Ulrich Zeidler, Düsseldorf, all of Fed. Rep. of Germany

[73] Assignee: Henkel Kommanditgesellschaft auf Aktien, Duesseldorf, Fed. Rep. of Germany

[21] Appl. No.: 831,373

[22] Filed: Feb. 20, 1986

Related U.S. Application Data

[60] Division of Ser. No. 563,949, Dec. 21, 1983, abandoned, which is a continuation-in-part of Ser. No. 340,066, Jan. 18, 1982, abandoned.

[30] Foreign Application Priority Data

Jan. 24, 1981 [DE]  Fed. Rep. of Germany ....... 3102373

[51] Int. Cl.$^4$ .................... A61K 31/41; A61K 31/535
[52] U.S. Cl. .................................. 514/384; 514/236.2
[58] Field of Search ......................................... 514/384

[56] References Cited

U.S. PATENT DOCUMENTS 4,283,546  8/1981  Rottmaier et al. ................. 548/264
4,467,099  8/1984  Giesecke et al. ................... 548/264

Primary Examiner—Jerome D. Goldberg
Attorney, Agent, or Firm—Ernest G. Szoke; Henry E. Millson, Jr.; Wayne C. Jaeschke

[57] ABSTRACT

N-substituted polyglycidyl urazole compounds of the general formula

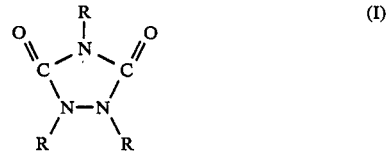

in which the radicals R represent a glycidyl radical corresponding to the following general formula

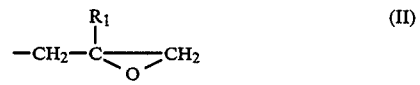

wherein $R_1$ represents hydrogen or an alkyl radical containing from 1 to 4 carbon atoms, or two of the radicals R represent a glycidyl radical of general formula II while the remaining radical R is a radical Z, other than said glycidyl radical, containing carbon, hydrogen and, optionally, heteroatoms, are useful in the treatment of various forms of leukemia.

7 Claims, No Drawings

N-SUBSTITUTED POLYGLYCIDYL URAZOLE COMPOUNDS, PROCESSES FOR THEIR PRODUCTION AND PHARMACEUTICAL PREPARATIONS

This is a division of copending Ser. No. 563,949, filed Dec. 21, 1983, now abandoned which was a continuation-in-part of Ser. No. 340,066, filed Jan. 18, 1982, now abandoned.

This invention relates to N-substituted polyglycidyl urazole compounds, processes for their production and use in pharmacy.

German Offenlegungsschrift No. 29 07 349, corresponding to U.S. patent application Ser. No. 95,229, filed Nov. 19, 1979, abandoned in favor of its continuation, Ser. No. 257,893, filed Apr. 27, 1981, abandoned in favor of its continuation-in-part Ser. No. 508,486, filed June 27, 1983, relates to cytostatically active pharmaceutical preparations containing as their pharmacologically active principle triglycidyl isocyanurate (TGI) and/or TGI derivatives in which the hydrogen atom of the carbon in the 2-position of the glycidyl group may be replaced by an alkyl radical containing from 1 to 4 carbon atoms. Compounds of this type are distinguished by the fact that the three N-atoms of the isocyanuric acid ring are substituted by epoxy-group-containing glycidyl radicals which may even be substituted in the 2-position by an alkyl radical containing from 1 to 4 carbon atoms.

German Offenlegungsschrift No. 30 37 094.6, corresponding to U.S. patent application Ser. No. 194,908, filed Oct. 7, 1980, now U.S. Pat. No. 4,393,060, relates inter alia to cytostatically active pharmaceutical preparations containing compounds corresponding to the following general formula

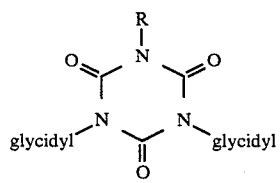

in which R may have the following meaning: alkyl, aryl, aralkyl, alkaryl, cycloalkyl, which radicals may, if desired, even be heterocyclic, unsaturated and/or substituted by at least one of the following substituents: halogen, hydroxyl, amino, N-substituted amino, mercapto, alkyl mercapto, aryl mercapto, alkyl sulfoxy, aryl sulfoxy, alkoxy, aroxy, acyloxy and heterocyclic radicals. The glycidyl radical has the meaning defined above.

The present invention is based on the observation that compounds of analogous structure, but derived from urazole as the parent substance, also show surprisingly strong antileukemia activity which can even exceed that of triglycidyl isocyanurate.

In a first embodiment, therefore, the present invention relates to new N-substituted polyglycidyl urazole compounds corresponding to the following general formula

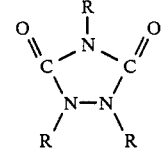

in which the radicals R represent a glycidyl radical corresponding to the following general formula

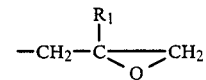

wherein $R_1$ represents hydrogen or a $C_1$–$C_4$-alkyl radical, or two of the radicals R represent a glycidyl radical of general formula II and the remaining radical R is a radical Z, other than said glycidyl radical, containing carbon, hydrogen and optionally heteroatoms.

In a first particularly preferred embodiment of the invention, the three radicals R present in N-substitution are a glycidyl radical corresponding to general formula II. In this connection, it is particularly preferred for $R_1$ to represent hydrogen in at least two of the glycidyl radicals and preferably in all the glycidyl radicals.

In the production of 1,2,4-triglycidyl urazole (TGU), three diastereomers are theoretically formed because only two of the three glycidyl groups have the same chemical surroundings.

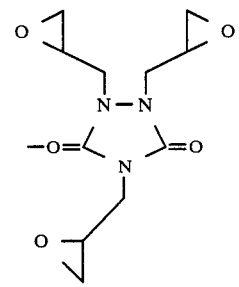

Statistically, the following isomer distribution should be obtained without any mutual influence:

| RRR' SSS' | SRR'≡RSR' RSS'≡SRS' | RRS' SSR' |
|---|---|---|
| 1 | : 2 | : 1 |
| (β) | (γ) | (α) |

These three isomers are present in the crude product obtained after the treatment with alkali. According to the results of column chromatography as described in the following, the TGU isolated as primary product from the column consists of only two diastereomers which are present in a ratio of approximately 1:1. Identification: HPLC: silica gel/methylene chloride+2.5% of methanol.

The two diastereomers, which it is intended to refer to as α- and β-TGU, differ only slightly in their retention times. α-TGU has a slightly shorter retention time than β-TGU. In the inverse system (mobile phase: water+1.32% of THF), the ratios are reversed and separation becomes slightly better so that this system may also be used for preparative separation. Much better separation is obtained by HPLC employing a column containing chemical combined octasilane (Sorbax®C8). The column has an effective length of 250 mm and a diameter of 4.6 mm. The eluate employed is water containing 1.32% by weight of tetrahydrofurane. This moving phase is conducted through the stationary phase at a pressure of 77 bar with a throughput of 2 ml/minute. By this method, βTGU is obtained in a purity of 90 to 95%.

α- and β-TGU also differ in their melting points and in their $^1$H-NMR-spectra—particularly significantly in the range from 4.0 to 4.4 ppm.

The third diastereomer, which it is intended to refer to as γ-TGU, was eluted from the column after the α-/β-TGU. It may also be isolated from the mother liquor after recrystallisation of the crude product obtained by the process described hereinafter by purification using column chromatography. This γ-TGU is liquid at room temperature and is present in the crude product in a proportion of from about 15 to 20% (and not 50% as had been expected).

The physical data of the three diastereomers are set out in the following Table.

TABLE

| TGU | M.p. or $n_D^{20}$: | $^1$H-NMR-double bands between 4 and 5 ppm (coupling const., Hz) | | | |
| --- | --- | --- | --- | --- | --- |
| α- | 104° C. (extrapol.) | 4.17 | (3.0); | 4.35 | (3.0) |
| β- | 115–116° C. (extrapol.) | 4.07 | (2.4); | 4.23 | (2.4) |
| γ- | 1.5088 | 4.55 | (2.5); | 4.66 | (2.5); |
| | | 4.08 | (6.3); | 4.18 | (6.3); |
| | | or as a double doublet | | | |
| | | 4.12 | (12.0); | 4.60 | (12.0) |

The integral of this range corresponds to approximately two protons.

The present invention also relates to these three diastereomers of 1,2,4-triglycidyl urazole, to the process for their production and to their use as described in the following. Mixtures of these diastereomers which differ in their composition from the diastereomer mixture originally obtained by synthesis also fall within the scope of the present invention. In this connection, the present invention relates in particular to diastereomer mixtures of TGU which consist essentially of two of the above-mentioned diastereomer types: Thus, the scope of the invention includes, in particular, the mixture consisting essentially of α- and β-TGU obtained by column chromatography and its use.

In another important embodiment of the invention, only two glycidyl radicals corresponding to general formula II are present in the urazole ring, while the third radical is a radical Z, other than said glycidyl radical, having the meaning defined above. In this case, too, it is preferred for the two glycidyl radicals in $R_1$ to contain hydrogen. In principle, Z may be any organic radical, other than said glycidyl radical, which, in addition to carbon and hydrogen atoms, may also contain heteroatoms. The heteroatoms in question are primarily O, N, S and/or P.

According to the invention, the molecular weight of a radical Z of the type in question preferably does not exceed the limits indicated below. Thus, the molecular weight of this radical Z is best no more than about 750 and, more particularly, no more than about 500. It can also be of advantage for the molecular weight of the radical Z not to exceed a value of approximately 300 or even a value of approximately 200.

In preferred embodiments of the invention, Z may have one of the following meanings: alkyl, aryl, aralkyl, alkaryl, cycloalkyl, which radicals may if desired even be heterocyclic, unsaturated and/or substituted by at least one substituent. The substituents in question are, in particular, halogen, hydroxyl, amino, N-substituted amino, mercapto, alkylmercapto, aryl mercapto, alkyl sulfoxy, aryl sulfoxy, alkoxy, aroxy, acyloxy and heterocyclic radicals. If Z contains a substituted radical, correspondingly substituted alkyl radicals may be preferred, although substituted aryl radicals and cycloalkyl radicals are not out of the question. Preferred unsaturated radicals are olefinically unsaturated radicals.

The present invention also relates to processes for producing the new N-substituted polyglycidyl compounds corresponding to general formula I and to pharmaceutical preparations characterised in particular by antileukemia activity and containing compounds corresponding to general formula I.

The mechanism by which the compounds used in accordance with the invention act has not been explained in detail. Presumably, the glycidyl groups which are present both here and in the triglycidyl isocyanurate according to DE-OS No. 29 07 349 are of crucial importance so far as the cytostatic effect is concerned. All the compounds of general formula I according to the invention are characterised by the presence of at least two such glycidyl groups. In addition, the widely variable radical Z may optionally be present in the class of compounds in question. It is possible that the distribution of lipophilic and hydrophilic preferences is influenced through this radical Z and that the absorption of the compounds by the organism may thus be controlled to a certain extent. However, the new substituent Z introduced in accordance with the invention is not limited in its meaning to this possible effect.

According to the foregoing definition, the radical Z is a hydrocarbon radical, other than said glycidyl radical, which may also contain heteroatoms. The heteroatoms in question are, in particular, N, O, S and/or P. This radical preferably contains in all no more than 15 carbon atoms, preferably no more than 12 carbon atoms and, more preferably, no more than 8 carbon atoms. Radicals containing up to 6 or, preferably, even only up to 4 carbon atoms may be particularly interesting. These figures should be interpreted independently of the particular structure and merely apply to the sum of all the carbon atoms in the radical in question.

If Z is an aryl, aralkyl or alkaryl radical, mononuclear substituents are particularly preferred in this case. Typical representatives are phenyl, benzyl, tolyl, xylyl and related compounds. In the case of the cycloaliphatic rings, mononuclear ring systems based on cyclopentyl, cyclohexyl and their derivatives are also preferred for the radical Z. Corresponding heterocyclic radicals, i.e. in particular mononuclear ring compounds containing O, N and/or S in the system, fall within the scope of the invention. The ring systems in question may preferably contain 1, 2 or 3 such heteroatoms. These heterocyclic radicals preferably contain 5 or 6 ring members. If desired, all the cyclic substituents mentioned here, whether aromatic or cycloaliphatic in nature, may in turn contain further substituents. Suitable substituents are, for example, halogen, hydroxyl or alkoxy.

In one particularly preferred embodiment of the invention, the radical Z represents an optionally substituted alkyl radical. This alkyl radical may be straight-chain or branched and saturated or unsaturated and, excluding its substituents, preferably contains no more than 10 carbon atoms and, more particularly, no more than 8 carbon atoms. In this embodiment of the invention, particular preference is attached to those compounds of general formula I in which the radical Z represents unsubstituted alkyl containing from 1 to 6 carbon atoms or a corresponding alkyl radical substituted by halogen, hydroxyl, amino, N-substituted amino, mercapto, alkyl mercapto, aryl mercapto, alkyl sulfoxy, aryl sulfoxy, alkoxy, aroxy and/or acyloxy; the substituent in question may even be heterocyclic by nature.

Radicals substituted in this way may be substituted once or several times by the above-mentioned groups. From 1 to 3 of the above-mentioned substituents are preferably present on the particular radical Z. In one particularly preferred case, compounds of general formula I containing substituted alkyl radicals of the above-mentioned type are used in the pharmaceutical preparations according to the invention.

In cases where substituting groups which, in turn, contain hydrocarbon radicals—i.e. in particular in the case of the radicals N-substituted amino, alkyl mercapto, aryl mercapto, alkyl sulfoxy, aryl sulfoxy, alkoxy, aroxy and acyloxy—are present on the substituted alkyl radical Z, these substituting groups preferably contain no more than 10 and best no more than 8 carbon atoms. The particularly preferred limit lies at 6 carbon atoms and, more particularly, at no more than 4 carbon atoms. These substituting hydrocarbon radicals may in turn be aryl, aralkyl, alkaryl, cycloalkyl and/or alkyl radicals which, if desired, may also contain such substituents as halogen, hydroxyl, alkoxy and the like. In this case, too, the radicals in question include radicals containing heteroatoms of the type mentioned above, i.e. for example heterocyclic ring systems containing from 1 to 3 heteroatoms of the type mentioned above, more particularly mononuclear rings containing N, O and/or S as heteroatoms. Corresponding 5-membered and 6-membered heterocycles are preferred.

One particularly preferred embodiment of the invention relates to compounds corresponding to general formula I in which one of the radicals R, i.e. the radical Z, represents a monosubstituted or disubstituted alkyl radical of the above-mentioned type selected from the following group: monohydroxy alkyl, dihydroxy alkyl, halogen hydroxy alkyl, N-substituted aminohydroxy alkyl, alkyl mercaptohydroxy alkyl, substituted alkyl mercaptohydroxy alkyl, the corresponding alkyl sulfoxy hydroxy alkyls, optionally substituted alkoxy hydroxy alkyl and, optionally, substituted acyloxy hydroxy alkyl. The alkyl radical may advantageously contain up to 7 carbon atoms, preferably from 3 to 7 carbon atoms and, more particularly, 3, 4 or 5 carbon atoms.

According to the invention, preferred compounds of general formula 1 may be those in which the radical Z represents straight-chain or branched unsubstituted alkyl containing up to 6 carbon atoms and preferably up to 4 carbon atoms. The radicals in question are, in particular, methyl, ethyl, propyl, isopropyl, the corresponding C4-radicals and their olefinically unsaturated analogs. In addition, compounds of general formula I in which one of the radicals R is a monosubstituted or disubstituted alkyl radical of the type mentioned above containing in particular 3 carbon atoms and preferably contains at least one hydroxyl group, are particularly preferred. In these compounds, therefore, at least one hydroxy group is always present, preferably adjacent another substituent on the radical in question, whilst the other two radicals R represent the glycidyl radical corresponding to general formula II. In another preferred embodiment of the invention, these substituting groups in the radical Z are distributed between the 2-position and the 3-position of the radical R in question. In this connection, the hydroxy group may be either in the 2-position or in the 3-position. Other particularly preferred, correspondingly substituted compounds of formula I contain no other substituting group apart from the hydroxyl group in the radical Z or contain as further substituents hydroxyl, halogen, an N-substituted amino radical, an optionally substituted alkoxy radical, an optionally substituted alkyl mercapto or alkyl sulfoxy radical or an optionally substituted acyloxy radical. Particularly preferred halogens are chlorine and/or bromine, although fluorine and iodine may also be considered. The N-substituted amino radicals may correspond to the formula

in which the radicals $R_2$ and $R_3$ represent hydrocarbon radicals which may in turn be substituted. In the preferred embodiment of the invention, these radicals $R_2$ and, if desired, $R_3$ contain up to 12 carbon atoms, the sum of the radicals $R_2$ and $R_3$ in the disubstitution on the nitrogen preferably not exceeding 12 carbon atoms. More preferably, these substituents $R_2$ and $R_3$ contain in all up to 8 carbon atoms and, more particularly, no more than 5 carbon atoms. The radicals $R_2$ and $R_3$ may even be closed together to form a saturated or unsaturated, optionally aromatic and/or heterocyclic ring. Preferably, $R_2$ and, optionally, $R_3$ may also be alkyl radicals. If these radicals are in turn substituted, the substituents in question in the context of the invention are, in particular, hydroxyl, alkoxy or halogen preferably chlorine or bromine. If, in addition to the hydroxy group, Z contains an acyloxy radical, an alkoxy radical or an alkyl mercapto or alkyl sulfoxy radical, this radical also preferably contains up to at most 10 carbon atoms, the preferred limit in this case, too, lying at 8 carbon atoms. It is particularly preferred to introduce no more than 5 carbon atoms into the molecule at this point. Alkyl radicals containing the corresponding number of carbon atoms are also preferred in the case of acyloxy radicals, although aryl radicals may also be considered. The acyloxy radicals are preferably derived from monocarboxylic acids having the above-mentioned number of carbon atoms and the above-mentioned structure.

The medicaments according to the invention may with advantage contain individual, defined compounds corresponding to general formula I, although it has been found that active-substance mixtures of several of the compounds falling within the scope of general formula I are also highly effective antileukemia agents. According to the invention, it can also be of advantage to use certain individual compounds or a mixture of several compounds corresponding to formula I in admixture with the TGI compounds disclosed in DE-OS No. 29 07 349 and in German Patent Application P 30 37 094.6.

The production of the compounds according to the invention may be carried out in several ways and is another subject of the present invention. 1. Introduction of the glycidyl groups of general formula II in N-substitution into the urazole ring. To this end, urazole, i.e. the parent compound of formula I containing an —NH— group instead of each of the N-glycidyl groups, is first produced in known manner. The hydrogen on the nitrogen atom is then replaced by the glycidyl group.

There are above all two fundamental possibilities for carrying out this final step of the reaction. One of these is directly to introduce the glycidyl group by reacting the NH-group with epihalohydrins, particularly epichlorohydrin or epibromohydrin, followed by dehydrohalogenation. The other possible method completes the formation of the molecule in the two reaction steps. Firstly, the corresponding allyl-substituted intermediate products are formed, after which the allyl group is epoxidised in a concluding step.

The reaction of —NH—groups with epihalohydrins is widely reported in the literature. The reaction may be carried out in the presence of a small quantity of a quaternary ammonium compound as catalyst (cf. for example Houben-Weyl "Methoden der Organischen Chemie", Vol. 14/2 (1963), 497, 547). Particularly suitable quaternary ammonium compounds belong to the class of phase transfer catalysts. The compounds in question are known to be quaternary ammonium compounds of pronounced lipophilic character attributable in particular to the presence of sufficiently large organic residues in the quaternary ammonium compound. Detailed information on phase transfer catalysts may be found for example in "Phase Transfer Catalysis in Organic Synthesis" by W. P. Weber and G. W. Gobel, Springer Verlag, Berlin, Heidelberg, New York, 1977 and in "Phase Transfer Catalysis" by E. V. Dehmlow and S. S. Dehmlow, Verlag Chemie, Weinheim, Deerfield Beach (Florida), Basel, 1980.

The phase transfer catalysts are preferably used in quantities of from about 0.1 to 10% by weight, more preferably in quantities of from 0.5 to 5% by weight and most preferably in quantities of from 0.5 to 3% by weight, based on the urazole compound. In the following reaction step, dehydrohalogenation—which to some extent is also brought about by excess epihalohydrin—is completed by the addition of bases, preferably alkali metal hydroxides.

In the second process, the urazole compound is not directly reacted with the epoxide compound. Instead, it is first reacted with allyl halides which, although corresponding to the glycidyl radical in the compounds of general formula I, contain an olefinic double bond instead of the epoxide group, after which the allyl-substituted urazoles formed are epoxidised. Epoxidation may be carried out in known manner using peracids. A related reaction is, for example, the reaction of cyanuric acid with allyl halides as described in U.S. Pat. No. 3,376,301. The epoxidation of allyl isocyanurates using peracids is described for example in Houben-Weyl loc. cit. Vol. 6/3, pages 385 et seq. It may be carried out for example in the presence of a small quantity of a quaternary ammonium compound as catalyst.

The reaction of the urazole or of the monosubstituted urazole compound (cf in this connection Section 3. below) with epihalohydrins or with allyl halides is best carried out at temperatures in the range from about 50° to 150° C. and preferably at temperatures in the range from about 70° to about 125° C.

The reaction may be carried out in an excess of the epihalohydrin compound as solvent or in polar aprotic solvents which partly dissolve at least one of the reactants and which are not reactive to the reactants. Particularly appropriate solvents are any of the dialkyl formamides, particularly the lower dialkyl formamides, such as dimethyl formamide. The preferred reaction time is from 1 to 10 hours and, more particularly, from 2 to 5 hours.

The complete dehydrohalogenation of the halohydrins formed as intermediates may be obtained by the addition of solid, powdered alkali, preferably NaOH, or by the addition of highly concentrated aqueous solutions. This dehydrohalogenation step is carried out either in excess epihalohydrin or after the removal thereof by distillation under reduced pressure in a polar aprotic solvent, such as for example dimethoxy ethane, diglyms or dimethyl formamide, at temperatures in the range from −10° to 60° C. and preferably at temperatures in the range from 0° to 45° C.

Epoxidation of the allyl groups using peracids is also preferably carried out in solvents. Solvents suitable for this purpose are, once again, polar solvents, for example halogenated hydrocarbons or alcohols.

Suitable reaction temperatures are normally in the range from 0° to 50° C. and, more particularly, in the range from about 10° to 30° C. The peracid is best used in a substantially equivalent quantity or in only a slight excess. m-chloroperbenzoic acid is readily available as a commercial product and suitable for carrying out the reaction. The reaction time is generally of the order of 24 hours or longer, for example up to 48 hours.

If unsubstituted urazole is used as starting material in these reactions, it is possible to obtain the triglycidyl-substituted urazoles. 2. There are various possibilities for producing urazole derivatives according to the invention in which two of the radicals R in general formula I represent a glycidyl radical and the third radical R represents the radical Z. One possibility is to react triglycidyl urazole (TGU) with a substoichiometric quantity of water, alcohol, primary and/or secondary amines, mercaptans, imines, imides, carboxylic acids, hydrogen halide and the like or hydrogen.

In view of the similarity of the three glycidyl groups in the TGU, this reaction always leads in the first instance to product mixtures which in turn show therapeutic activity. However, it is also possible and part of the process according to the invention as described in the following to separate the corresponding compounds of general formula I from these mixtures by suitable separation techniques, for example by preparative thin-layer chromatography or column chromatography.

In the curse of these reactions, a glycidyl group is converted into the radical Z of the compounds corresponding to general formula I. A monohydroxyalkyl radical Z is formed in the reductive treatment of the glycidyl group with hydrogen or with hydrogen donors. Suitable hydrogen donors are, for example, hydride compounds, for example complex borohydrides, such as sodium borohydride. In the other cases mentioned, the triglycidyl starting compound is reacted with a substoichiometric quantity of a nucleophilic compound $H^+A^-$, resulting in the formation of a disubstituted radical Z which, in addition to a hydroxyl group, contains the radical $A^-$ as a second substituent, normally on the atom adjacent the hydroxylated C-atom of the radical R.

The reaction of the glycidyl groups of a structurally similar compound, namely triglycidyl isocyanurate(TGI), with nucleophilic reactants of the type in question is state of the art and is described, for example, in Angew. Chemie 80, 851 (1968). In the prior art, however, this reaction is specifically carried out on more than only one epoxide group of the TGI and is used for example in the crosslinking of epoxide resin systems on an industrial scale. By contrast, the process according to the invention is preferably carried out under conditions which enable the yield to be increased as far as possible towards 1:1 reaction products and which provide for the subsequent isolation and recovery of these 1:1 reaction products by separating off unreacted parts of the starting material and more advanced reaction products which have formed through the reaction of more than only one epoxide group with the nucleophilic reactant.

In the reaction of TGU-compounds with nucleophilic reactants $H^+A^-$ of the type mentioned above, it may be difficult to obtain the required 1:1 reaction products in high yields because the three epoxide groups of the molecule of the starting compound are substantially equal to one another in their reactivity, with the result that in many cases the required diglycidyl compound is not formed as the main reaction product. Difficulties are also occasionally involved in efforts to increase the concentration of the required compound by reacting the triglycidyl urazole with a substoichiometric quantity of nucleophilic reactant.

It has been found that the 1:1 reaction products can be produced surprisingly easily by reacting the triglycidyl urazole with an excess and preferably with a large excess of the nucleophilic reactant $H^+A^-$, but prematurely terminating the reaction and separating off the excess of nucleophilic reactant, unreacted TGU and co-formed diaddition and triaddition products. The crude diglycidyl product left behind may then be purified by conventional methods, for example by column chromatography. In this process, the nucleophilic reactant is preferably used in a 3- to 30-fold excess and, more particularly, in a 5- to 20-fold excess over and above the necessary quantity. The reaction may be carried out in solvents although, if desired, the excess of the nucleophilic reactant may also serve as solvent. If the reaction is carried out in solvents, the solvents used are best substantially polar solvents which, preferably, are not reactive under the conditions selected for the process. The solvent may also be immiscible with water. Particularly suitable solvents are, for example, halogenated hydrocarbons, particularly chlorinated hydrocarbons. The reaction temperature is normally in the range from about 30° to 120° C. and preferably in the range from 40° to 100° C. and, in one particularly suitable embodiment, is selected in such a way that the epoxide content of the reaction mixture falls by half in 4 to 5 hours.

Both in this process and in the other processes described in the following, the purification of the 1:1 reaction product containing two epoxide groups and its recovery from the mixture of reactants is generally an essential step of the process according to the invention. For the production of the sulfoxy compounds from the corresponding mercapto compounds, see Houben-Weyl loc. cit., Vol. 9 (1955), pages 207–217 and Makromol. Chem. 169, 323(1979). 3. An extremely elegant, general process for producing the compounds corresponding to general formula I is based on the reaction of the mono-N-substituted urazole compound with epihalohydrins. The production of mono-N-substituted urazole may be carried out by methods known from the literature. For relevant literature, see for example Org. Synthesis, Vol. 51, 121 (1971).

The substituent introduced into the urazole generally corresponds to the radical Z in the compounds of general formula I. The two glycidyl groups are then introduced in a subsequent reaction. To this end, the monosubstituted urazole is reacted with the corresponding epihalohydrin compound, for example with epichlorohydrin, followed by dehydrohalogenation, or with allyl halide, followed by epoxidation of the double bond, as described above in section 1. with reference to the triglycidyl urazole.

In another embodiment, therefore, the present invention relates to a process for the production of N-substituted polyglycidyl urazole compounds corresponding to the following general formula

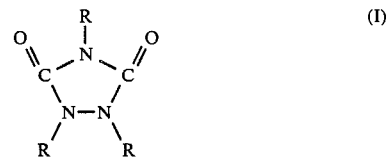

in which R is as defined above, characterised in that the two glycidyl radicals corresponding to general formula II are introduced in N-substitution into urazole or into a urazole mono-N-substituted by the radical Z or a triglycidyl urazole containing a glycidyl radicals corresponding to general formula II is subjected to a partial reaction with water, alcohols, compounds containing a primary or secondary amino group, mercaptans, hydrogen sulfide, carboxylic acids, hydrogen halide or hydrogen or hydrogen donors, the thio compounds formed are, if desired, converted into the corresponding sulfoxy compounds and the reaction products formed, which correspond to general formula I, are separated off from the reaction mixture and recovered as such.

If, in this process, the glycidyl radicals corresponding to general formula II are introduced into urazole or into mono-N-substituted urazole, this may be done by directly reacting the urazole compound optionally substituted by the radical Z with epihalohydrins, these epihalohydrin compounds corresponding to the glycidyl radicals of general formula II, followed by dehydrohalogenation, or alternatively by initially reacting the urazole compounds with corresponding allyl halides and subsequently converting the allyl radicals or the allyl radicals substituted by $R_1$ into the glycidyl group by epoxidation, preferably using peracids. All the observations made in the foregoing apply in the same way to the characteristics of the compounds corresponding to general formula I, the radicals R and Z and glycidyl and the reactants involved in their formation.

The compounds corresponding to general formula I, particularly in purified form and in bulk, are new compounds. They are suitable for use in medicaments. However, the new polyglycidyl urazole compounds may also be used in other fields where polyglycidyl-substituted compounds normally occupy a position of importance. Fields of this type are known to include in particular the field of plastics and, more particularly, the field of epoxide resins.

If the polyglycidyl compounds contain a radical Z in addition to two glycidyl radicals of general formula II, this radical Z may be in the 1-, 2- or 4-position. The 4-position may be particularly important for these compounds containing the radical Z, above all on preparative grounds.

Finally, the present invention also relates to the use of the compounds corresponding to general formula I for the treatment of leukemia, including a reduction in the number of P388 (Leukemia) tumor type cells in mice. The compounds may be administered in individual doses of from 1 to 200 mg/kg. Certain individual compounds corresponding to general formula I or mixtures thereof may be used. Their use in admixture with other active components, for example TGI, also falls within the scope of the present invention.

The compounds of general formula I used in accordance with the invention occur in various stereoisomeric forms. In principle, any of these various forms are suitable for the purposes of the invention. In this connection, they may be used either in admixture or even in the form of certain isolated isomers.

For use as antileukemia agents, the active substances should be applied by means of suitable vehicles. Suitable vehicles are the auxiliaries and excipients normally used for pharmacological preparations. In the present case, suitable vehicles are aqueous systems, optionally in conjunction with compatible ethylene glycol ethers, such as glycol monoethyl ether or butylene glycol methyl ether or propylene glycol methyl ether, particularly if the active principle is to be administered parenterally. In the case of oral administration, the usual pharmaceutical auxiliaries and vehicles may be used, providing they are sufficiently compatible with the glycidyl compounds.

In animal experiments, good results were obtained with freshly prepared aqueous solutions administered i.p. or i.v.

The compounds used in accordance with the invention are effective against various forms of leukemia. In some cases, the new urazoles were found to be distinctly superior to cyclophosphamide and fluoruracil.

Combination therapy in conjunction with other cytostatic agents, such as derivatives of nitrogen mustard gas or even fluoruracil, is possible.

It may be said quite generally of the compounds of general Formula I containing a radical Z used in accordance with the invention that this radical Z shows or should show little or no reactivity with the epoxide groups of the glycidyl substituent(s) on the ring system of general formula I, at least under normal conditions or at least with cooling.

This ensures that the active components used in accordance with the invention are sufficiently stable in storage and do not undergo any undesirable reaction culminating in destruction of the epoxide groups. This rule should also be observed in particular in the selection of any substituents present on the radical R.

The following are examples of the radical Z in the antileukemia active compounds of general formula I used in accordance with the invention: methyl, ethyl, propyl, butyl, pentyl, hexyl, the corresponding isomeric radicals, such as isopropyl, isobutyl, tert.-butyl, isopentyl, corresponding unsaturated radicals, particularly olefinically unsaturated radicals, such as vinyl, allyl, butenyl, phenyl, benzyl, xylyl, trimethyl phenyl, isopropyl phenyl, naphthyl, cyclopentyl, cyclohexyl, the corresponding cycloaliphatic radicals substituted by 1 to 3 alkyl or alkenyl radicals, the alkyl or alkenyl substituents preferably containing from 1 to 4 carbon atoms, 2,3-dihydroxypropyl, 2-hydroxy-3-diethylaminopropyl, 2-hydroxy-3-dimethylaminopropyl, 2-hydroxy-3-(dihydroxyethylamino)-propyl, 2-hydroxy-3-morpholinopropyl, 2-hydroxy-3-phenoxypropyl, 2-hydroxy-3-methoxypropyl, 2-hydroxy-3-ethoxypropyl, 2-hydroxy-3-propoxypropyl, 2-hydroxy-3-acetoxypropyl, 2-hydroxy-3-propyloxypropyl, 2-hydroxy-3-butyloxypropyl, 2-hydroxy-3-(3-carboxypropyloxy)propyl, 3-hydroxy-2-acetoxypropyl, 3-hydroxy-2-propyloxypropyl, 3-hydroxy-2-butyloxypropyl, 3-hydroxy-2-(3-carboxypropyloxy)-propyl, 2-hydroxy-3-chloropropyl and 2-hydroxy-3-bromopropyl.

The following are additional examples of the possible meanings for R which fall within the scope of the invention: halogen alkyl in general, hydroxyalkyl thiopropyl, 2-hydroxy-3-methylaminopropyl, 2-hydroxy-3-ethylaminopropyl, 2-hydroxy-3-di-($\beta$-chloroethyl)-aminopropyl, 2-hydroxy-3-benzyloxypropyl and 2-hydroxy-3-hydroxypropyloxypropyl. Other possible meanings for the radical R are 2-hydroxy-3-methyl thiopropyl, 2-hydroxy-3-butyl thiopropyl, 2-hydroxy-3-phenyl thiopropyl, 2-hydroxy-3-(benzoxazol-2'-ylthio)-propyl, 2-hydroxy-3-acetothiopropyl, 2-hydroxy-3-octylthiopropyl, 2-hydroxy-3-(2',3'-dihydroxypropyl-thio)-propyl, 2-hydroxy-3-(benzimidazol-2'-ylthio)-propyl, 2-hydroxy-3-(benzthiazol-2'-ylthio)-propyl.

In the context of the invention, suitable reactants for converting a glycidyl group in the triglycidyl urazole to form a substituted radical Z are, quite generally, alkanols, such as methanol, ethanol, n-propanol, isopropanol, n-butanol, isobutanol, sec.-butanol, tert.-butanol, 1-pentanol, 2-pentanol, 3-pentanol, 2-methyl-1-butanol, 3-methyl-1-butanol, 2-ethyl-2-butanol, 3-methyl-2-butanol, 2,2-dimethyl-1-propanol, 1-hexanol, 2-ethyl-1-butanol, 4-methyl-1-pentanol, 4-methyl-2-pentanol, 2-methyl-1-pentanol. Suitable unsaturated alcohols are, for example, 2-buten-1-ol, 2-propyn-1-ol, allyl alcohol, crotyl alcohol, 3-buten-2-ol, 2-buten-1-ol and 3-butyn-2-ol. Examples of polyhydric alcohols are ethylene glycol, 1,2-propane diol, 1,3-propane diol, 1,4-butane diol, 1,2-butane diol, 2,3-butane diol, 1,3-butane diol, 2-butene-1,4-diol, 2-butyne-1,4-diol, 1,5-pentane diol, 2-methyl-1,4-butane diol, 2,2-dimethyl-1,3-propane diol, hexane diol, 2,5-dimethyl-3-hexyne-2,5-diol, glycerol, 1,2,4-butane triol, 2-hydroxymethyl-2-ethyl propane diol, 2-methyl-2-hydroxymethyl-1,3-propane diol, pentaerythritol. Examples of thiols in this connection are methane thiol, ethane thiol, 1-propane thiol, 2-propane thiol, 2-methyl-2-propane thiol, 2-butane thiol, 2-methyl-1-propane thiol, 1-butane thiol, 1-pentane thiol, 1-hexane thiol and 1,2-ethane thiol, 2,2-propane thiol, benzene thiol, p-benzene dithiol, pyridine-2-thiol and thiophene-2-thiol. The sulfoxide compounds obtained from mercapto radicals of this type fall within the scope of the invention. Examples of carboxylic acids are, in particular, acetic acid, propionic acid, n-butyric acid, n-valeric acid, capric acid, oenanthic acid, isobutyric acid, 3-methyl butanoic acid, 2,2-dimethyl propanoic acid, 2-methyl butanoic acid, 2-ethyl butanoic acid, 2-ethyl hexanoic acid. Unsaturated acids are, for example, propenoic acid, 2-methyl propenoic acid, 3-methyl propenoic acid, 2,3-dimethyl propenoic acid, hexadienoic acid, propiolic acid. Examples of substituted acids are 2-chloropropanoic acid, 3-chloropropanoic acid, 2,2-dichloropropanoic acid, 2,3-dichloropropanoic acid, 3,3-dichloropropanoic acid, 2,2,3,3,3-pentachloropropanoic acid, 2-chlorobutanoic acid, 3-chlorobutanoic acid, 4-chlorobutanoic acid, 2-chloro-2-methylpropanoic acid, 3-chloro-2-methylpropanoic acid, 2,3-dichlorobutanoic acid, 2,2,3-trichlorobutanoic acid, 2-chloropentanoic acid, 3-chloropentanoic acid, 4-chloropentanoic acid, 5-chloropentanoic acid, 2- chloro-2-methylbutanoic acid, 2-chloro-3-methylbutanoic acid, 3-chloro-2,2-dimethylpropanoic acid. Examples of aromatic acids are benzoic acid, phthalic acid, isophthalic acid, terephthalic acid and the corresponding acids substituted by methyl or ethyl radicals. Further examples of substituted acids are glycolic acid, hydroxybutyric acid (α,β and γ-forms), hydroxybenzoic acid with the hydroxy group in the o-, m- or p-position, hydroxybenzoic acid with the hydroxy groups in the 3,4-, 2,3-, 2,4-, 3,5- or 2,5-position, α-hydroxyphenylacetic acid. Phenolic compounds are, for example, phenol, α- and β-naphthol, cresols, xylenols, chlorophenols, chlorocresols, chloroxylenols, methyl phenols optionally containing more than one methyl group, for example 2,3,4-trimethyl phenol, ethyl phenols, propyl phenols, butyl phenols and the like. Examples of the reaction of the glycidyl group with amines are methylamine, dimethylamine, ethylamine, diethylamine, n-propylamine, di-n-propylamine, isopropylamine, diisopropylamine, n-butylamine, di-n-butylamine, sec.-butylamine di-sec.-butylamine, isobutylamine, diisobutylamine, tert.-butylamine, n-amylamine, di-n-amylamine, sec.-n-amylamine, isoamylamine, diisoamylamine, allylamine, diallylamine, cyclohexylamine, N-methylcyclohexylamine, dicyclohexylamine, cyclooctylamine. Examples of cyclic compounds containing amino groups are piperidine, hexamethylene imine, morpholine, aniline, α- and β-naphthylamine.

The polyglycidyl-substituted urazoles according to the present invention are normally present in the medicament mixtures according to the invention in concentrations of up to about 20% by weight, based on the medicament mixture. The concentration range from 0.05 to 10% by weight for example is suitable, the range from 0.05 to 5% by weight being particularly suitable.

The percentages quoted in the following Examples are percentages by weight, unless otherwise indicated.

EXAMPLES

EXAMPLE 1

15.2 g (0.15 mole) of urazole, 0.4 g of tetramethyl ammonium bromide and 0.5 g of Benzalkon A (a mixture of alkyl benzyl dimethyl ammonium chlorides) were boiled under reflux for 3 hours in 416 g (4.5 moles) of epichlorohydrin. After cooling, 28.8 g (0.72 mole) of powdered sodium hydroxide were added to the solution, followed by stirring for 6 hours at 45° C. The solution was then filtered off under suction from the deposit and evaporated to dryness under reduced pressure at 40° C., after which the residue was dissolved in a little methylene chloride and subjected to column chromatography (eluent-methylene chloride:methanol 95:5) on silica gel (Merck).

The individual fractions were combined after TC-analysis. After concentration by evaporation, the second collective fraction (substance with the second highest $R_F$-values) yielded 1.5 g of 1,2,4-triglycidyl urazole which, after recrystallisation from ethyl acetate, still melted at 93° to 94° C.
Epoxide number observed: 17.1
calculated: 17.8

The structure is confirmed by elemental analysis and mass spectrum. This product is a mixture of stereoisomers in a ratio of α:β:γ of about 5:5:2.

EXAMPLE 2

1.53 g (0.01 mole) of 4-phenyl urazole (prepared in accordance with Org. Syntheses, Vol. 51, page 121 (1971)), 0.08 g of Benzalkon A, 0.08 g of tetraethyl ammonium bromide and 50 g of epichlorohydrin are stirred for 4.5 hours at 60° C. After cooling to room temperature, followed by the addition of 20 g of molecular sieve 4 Å, 0.88 g (0.024 mole) of NaOH in 1 ml of $H_2O$ is added dropwise, after which the reaction mixture is stirred for 1.5 hours at 45° C., filtered under suction and concentrated in vacuo at 40° C.
Yield: 2.75 g
% EPO: 8.9

The crude reaction product is separated by column chromatography.
Column height: 40 cm, diameter; 4 cm
Filling: silica gel 60 (Merck)
Eluent: methylene chloride:ethylacetate:methanol 3:2:1.

The zone having an $R_F$-value of 0.65 is isolated. 1.85 g of 1,2-diglycidyl-4-phenylurazole are obtained.
% EPO: 11.9 (theoretical 12.1)

The structure is confirmed by the mass, IR- and NMR-spectra.

EXAMPLE 3

The following tests were carried out in accordance with the procedures laid down by the National Cancer Institute, Bethesda, Md. 200014, as published in "Cancer Chemotherapy Reports" Part 3, September 1972, Vol. 3, No. 2. The glycidyl compounds according to Examples 1 and 2 were used as active substances. The substance was freshly prepared in the form of an aqueous 1% injection solution immediately before application.

Tumor type P 388 (leukaemia) was induced i.p. in mice ($10^6$ cells/mouse) in accordance with procedure 1200 (page 91c). The average period of survival of the untreated animals is determined.

In further groups of tests, the active substance is administered to correspondingly pretreated animals. The life of the treated test animals is significantly prolonged by comparison with the average period of survival of the animals which have not been treated with the active substance. The prolongation factor T/C in dependence upon the dosage of the active substance is shown in the following

TABLE

| Example | Dose administered (mg/kg) | T/C-value |
| --- | --- | --- |
| 1 | 50 | 298 |
|   | 25 | >260 |
|   | 12.5 | 230 |
|   | 6.25 | 180 |
| 2 | 200 | 200 |
|   | 100 | 150 |
|   | 50 | 120 |
|   | 25 | 120 |

EXAMPLE 4

N-dihydroxypropyl-N',N"-diglycidyl urazole 5 g of triglycidyl urazole (0.019 mole) are stirred for 3 hours at 70° C. in 50 ml of water. The solution is concentrated in a rotary evaporator and dried in a high vacuum. The colourless, oily crude product (5.8 g) is purified by column chromatography.
Column: 35×5 cm.
Filling: silica gel 60; 0.063–0.2 mm(Merck).
Eluent:
    ethyl acetate: 2 parts.

methylene chloride: 2 parts.
methanol: 1 part.

The desired compound is obtained in the form of a colourless oil. Rf: 0.43 in the above eluent on silica gel plates
Yield: 30% by weight, based on crude product.
% epoxide oxygen: 11.02 (calculated 11.14).
IR, MS and $^1$H-NMR confirm the structure.

EXAMPLE 5

N-(2-hydroxy-3-propionoxy propyl)-N',N''-diglycidyl urazole 5 g of triglycidyl urazole (0.019 mole) and 14 g of propionic acid (0.19 mole) are stirred for 3 hours at 100°-110° C. in 100 ml of absolute toluene to which 5 g of moleculaar sieve 4 Å have been added. After filtration of the molecular sieve, the solution is concentrated. The residue is dissolved in methylene chloride and extracted by shaking twice with 50 ml of 10% soda solution. The methylene chloride phase dried over sodium sulfate is concentrated. The colourless oily residue obtained (5.2 g) is purified by column chromatography.
Column: 35×5 cm.
Filling: silica gel 60 (Merck) 0.063-0.2 mm.
Solvent: methylene chloride+5% methanol.

The desired compound is isolated in the form of a colourless oil.
Yield: 21% by weight.
Rf: 0.3 in the above-mentioned eluent on silica gel plates.
% epoxide oxygen: 9.5 (calculated 9.3).
IR and $^1$H-NMR confirm the structure.

EXAMPLE 6

N-(-2-hydroxy-3-morpholin-N-yl-propyl)-N',N''-diglycidyl urazole 5 g of triglycidyl urazole (0.019 mole) and 2 ml of morpholine (0.022 mole) are stirred for 3 hours at 50° C. in 100 ml of absolute isopropanol. The solution is concentrated and dried in a high vacuum. The yellowish, oily crude product (7.4 g) is purified by column chromatography.
Column: 35×5 cm.
Filling: silica gel 60 (Merck) 0.063-0.2 mm. Eluent: methylene chloride+20% of methanol.

The desired compound is isolated in the form of a colourless oil.
Yield: 51% by weight.
Rf: 0.72 in the above-mentioned eluent on silica gel plates.
% epoxide oxygen: 9.0 (calculated 9.0).
IR and $^1$H-NMR confirm the structure.
Elemental analysis:

|   | Observed | Calculated |
|---|----------|------------|
| C: | 50.7% | 50.55% |
| H: | 6.2% | 6.79% |
| N: | 15.5% | 15.72% |

EXAMPLE 7

1,2-diglycidyl-4-methyl-urazole 8.5 g (0.074 mole) of 4-methyl urazole (prepared in accordance with R. C. Cookson, S. S. Gupte et al., Org. Synth. 51 (1971), page 121) and 2% of tetraethyl ammonium bromide are stirred for 4 hours at 80° C. in 230 ml of epichlorohydrin (2.95 moles). After the addition of 65 g of molecular sieve 4 Å, the cooled solution is stirred for 3 hours at 40°-50° C. with 24 g of 50% sodium hydroxide (0.3 mole). After filtration under suction, the filtrate is concentrated by evaporation and the pale yellow, solid residue recrystallised from methanol. The 4.5 g (27% of the theoretical) of white crystals obtained, which have an epoxide oxygen content of 14% (calculated 14.1%), melt at 90° C. IR, $^1$H-NMR and MS confirm the structure.

EXAMPLE 8

1,2-diglycidyl-4-butyl urazole

The procedure is as in Example 7, except that 4-butyl urazole is used as the starting material. The crude product is purified by column chromatography.
Column: 40×5 cm.
Filling: silica gel 60 (Merck) 0.063-0.2 mm.
Eluent: methylene chloride +5% of methanol.

36% by weight of pure product are isolated.
Rf: 0.65 in the above-mentioned eluent on silica gel plates.
% epoxide oxygen: 11.7 (calculated 11.9).
M.P. of the white crystals: 49°-52° C.
IR and $^1$H-NMR confirm the structure.

EXAMPLE 9

The three stereoisomeric forms of triglycidyl urazole ($\alpha$-, $\beta$- and $\gamma$-isomer) are prepared and isolated as follows:

A mixture of 12.5 g (0.124 mole) of urazole, 174 g (1.88 mole) of epichlorohydrin and 0.25 g of tetraethyl ammonium bromide was stirred for 14 hours at 70° C., the volatile constituents were distilled off under reduced pressure at a bath temperature of 40° C., the residue was taken up in 300 ml of methylene chloride, and the solution filtered, followed by the addition over a period of 5 minutes with vigorous stirring at 20° C. of 70 g of a 30% sodium hydroxide solution. Stirring is continued for 1 hour at 20° C., after which the methylene chloride phase is separated off and the aqueous phase extracted three times with 100 ml of methylene chloride. The methylene chloride phases collected were concentrated by evaporation under reduced pressure (ultimately at around 1 mbar) at a maximum bath temperature of 40° C. The yield amounted to 23.2 g (69% of the theoretical). TGU is present in the form of a mixture of the three diastereomers (partly crystalline product) which, according to quantitative TC-analysis, contained 73% of $\alpha$-/$\beta$-TGU and approximately 15% of $\gamma$-TGU.

Recrystallisation from ethyl acetate gave $\alpha$-/$\beta$-TGU melting at 92°-97° C. (sintering at 87° C.) in a yield of approximately 40% (composition: $\alpha$-/$\beta$-TGU=50:50 (HPLC)). Further recrystallisation produced a gradual increase in the melting point to near the melting point of pure $\beta$-TGU.

The first mother liquor contained all the $\gamma$-TGU and some of the $\alpha$-/$\beta$-mixture. The $\gamma$-TGU was obtained in a yield of 10% from the mother liquor by column chromatography (silica gel/CH$_2$Cl$_2$:CH$_3$OH=98:2). $\gamma$-TGU is a colourless liquid having a refractive index $n_D^{20}$ of 1.5088. This $\gamma$-TGU was obtained with a purity of about 95%.

The $\alpha$-/$\beta$-mixture obtained from the first mother liquors contained distinct concentrations of $\alpha$-TGU. For the preparation of 90 to 95% pure $\beta$-TGU, the so-called "reversed phase column chromatography" was carried out. It is generally referred to as HPLC, as an abbreviation of "high pressure liquid chromatography". In the present case, the separation was effected on a column which contained chemically combined octasilane. It was purchased from DuPont under the name "Sorbax ®C 8". The column had an effective internal length of 250 mm and a diameter of 4.6 mm. The eluant used was water which contained 1.32% by weight of tetrahydrofurane. This moving phase was conducted through the stationary phase at a pressure of 77 bar. The throughput was 2 ml/min. The fractions were collected and the purity was evaluated with reference to the H-NMR spectrum. The IR spectra of the β-TGU had their maxima at 1 774 cm$^{-1}$ as well as 1 714 and 1 465/22 cm$^{-1}$. For commercial separation the mixed stereoisomers were separated as described on page 4, lines 25 to 35 of the specification. The α-TGU fraction was obtained with a purity of about 75%, with the remainder primarily β-TGU. The β-TGU fraction was obtained with a purity of about 75%, with the remainder primarily α-TGU. The γ-TGU fraction was obtained with a purity of about 95%.

As described in Example 3 experiments were carried out in mice with different compounds and the following results were obtained:

| Compound | Dose Administered mg/kg | T/C Value |
| --- | --- | --- |
| β-TGU fraction* | 50 | >300 |
| γ-TGU fraction | 100 | 293 |
|  | 50 | up to 210 |
| α-TGU fraction | High activity at less than 50 mg/kg | |
| Example 4 | 100 | >300 |
|  | 50 | 278 |
| Example 5 | 100 | 250 |
|  | 50 | 230 |
| Example 6 | 200 | 230 |
|  | 100 | 160 |
| Example 7 | 100 | >300 |
|  | 50 | 210 |
| Example 8 | 200 | 243 |
|  | 100 | 180 |
|  | 50 | 153 |

*All mice were healed.

We claim:

1. A method for treating leukemia in a warmblooded animal, including a human, comprising administering to said animal an N-substituted polyglycidyl urazole compound having the formula:

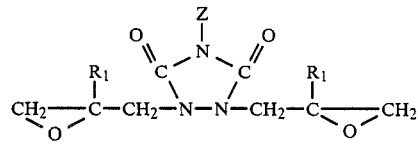

wherein Z is

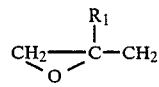

or a substituent which is $C_1$–$C_6$ alkyl, phenyl, dihydroxypropyl, 2-hydroxy-3-propionoxy propyl, or 2-hydroxy-3-morpholin-N-yl-propyl, and $R^1$ is hydrogen or $C_1$–$C_4$ alkyl; in an amount sufficient to inhibit leucocytic proliferation.

2. A method in accordance with claim 1 wherein $R_1$ is hydrogen.

3. A method in accordance with claim 1 wherein the urazole compound is 1,2,4-triglycidyl urazole.

4. A method in accordance with claim 1 wherein the urazole compound consists essentially of β-1,2,4-triglycidyl urazole.

5. A method in accordance with claim 1 wherein the urazole compound consists essentially of α-1,2,4-triglycidyl urazole.

6. A method in accordance with claim 1 wherein the urazole compound consists essentially of γ-1,2,4-triglycidyl urazole.

7. A method in accordance with claim 1 wherein the urazole compound is a mixture of the α- and β-isomers of 1,2,4-triglycidyl urazole.

* * * * *